United States Patent
Jackson et al.

(10) Patent No.: US 8,305,096 B2
(45) Date of Patent: Nov. 6, 2012

(54) APPARATUS AND METHOD FOR MEASURING AND MONITORING LAYER PROPERTIES IN WEB-BASED PROCESSES

(75) Inventors: Warren Jackson, San Francisco, CA (US); Carl Taussig, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1386 days.

(21) Appl. No.: 11/590,349

(22) Filed: Oct. 30, 2006

(65) Prior Publication Data

US 2008/0100302 A1     May 1, 2008

(51) Int. Cl.
 *G01R 27/08* (2006.01)
(52) U.S. Cl. ........ 324/716; 324/713; 324/715; 324/717; 324/718
(58) Field of Classification Search .............. 324/525, 324/713–718; 438/17, 18
See application file for complete search history.

(56) References Cited

U.S. PATENT DOCUMENTS

| | | | | |
|---|---|---|---|---|
| 3,936,738 | A * | 2/1976 | Maltby | 324/716 |
| 4,006,063 | A * | 2/1977 | Ensanian | 324/717 |
| 4,133,722 | A * | 1/1979 | Ensanian | 324/71.1 |
| 4,667,149 | A * | 5/1987 | Cohen et al. | 324/716 |
| 5,223,797 | A * | 6/1993 | Mayer et al. | 324/688 |
| 5,602,488 | A * | 2/1997 | Mikumo et al. | 324/716 |
| 7,106,077 | B2 * | 9/2006 | Kaz et al. | 324/715 |

* cited by examiner

*Primary Examiner* — Timothy J Dole

(57) ABSTRACT

An apparatus and method for measuring and monitoring layer properties in web-based processes are described. The apparatus includes multiple electrode devices adjacently positioned on a surface of a web material, which advances with a predetermined speed. The electrode devices perform measurements of electrical parameters of a layer of the web material and provide an electrical signal to a layer deposition system for further adjustment of layer properties of the layer.

21 Claims, 6 Drawing Sheets

APPARATUS AND METHOD FOR MEASURING AND MONITORING LAYER PROPERTIES IN WEB-BASED PROCESSES

BACKGROUND

1. Field of the Invention

The present invention relates generally to manufacturing technologies for electronic devices and, more specifically, to an apparatus and a method for measuring and monitoring layer properties in web-based processes.

2. Background

Over the last decades, progress in semiconductor manufacturing technology has centered on technology for increasing the scale of integration. Until recently, the process of photolithography on crystal and silicon wafers, where the desired structure is created by projecting a mask photolithographically onto a photo resist, has been the dominant semiconductor manufacturing process. However, photolithography is expensive for microfabrication processes involving large-area electronic devices, microelectromechanical (MEMS), and mechanical structures.

Web-based microfabrication is an emerging cost-effective manufacturing technology for such electronic devices, such as, for example, large area displays, solar cells, and/or touch sensitive surfaces, which relies on continuous imprinting of a desired pattern onto the photo resist, thus enabling elimination of start-up and stop times associated with traditional fabrication and ensuring higher quality and lower cost processing. However, web-based microfabrication technology requires accurate monitoring of layer properties.

What is needed is an apparatus and a method for measuring and monitoring layer properties in web-based processes, such as, for example, electrical resistance and capacitance parameters, and layer thickness, compositions, and impurities.

SUMMARY

An apparatus and method for measuring and monitoring layer properties in web-based processes are described. In one embodiment, the apparatus includes multiple electrode devices adjacently positioned on a surface of a web material, which advances with a predetermined speed. The electrode devices perform measurements of electrical parameters of a layer of the web material and provide an electrical signal to a layer deposition system for further adjustment of layer properties of the layer.

DETAILED DESCRIPTION

Figure 1:
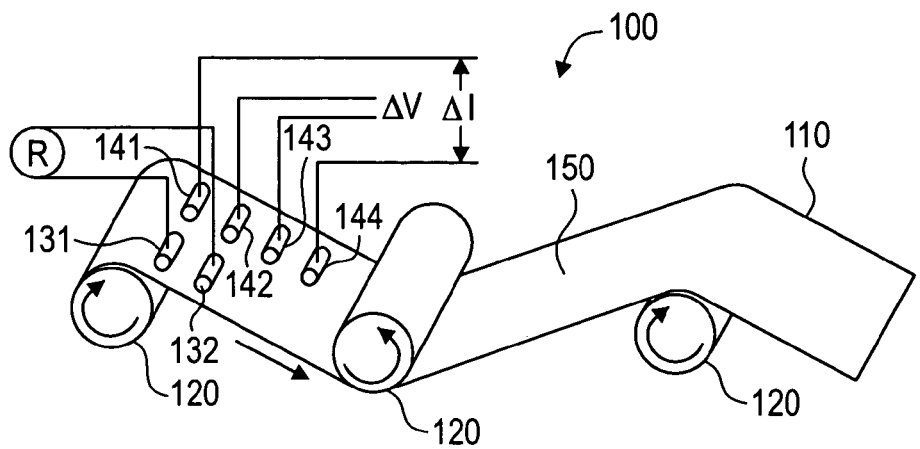
FIG. 1 illustrates a perspective view of a system for measuring and monitoring layer properties in web-based processes, according to one embodiment of the invention.

FIG. 1 illustrates a perspective view of a system for measuring and monitoring layer properties in web-based processes, according to one embodiment of the invention. As illustrated in FIG. 1, the system 100 includes a web material 110 and several conveyor modules 120 positioned to turn and advance the web material 110 in the direction of the arrow. In one embodiment, the system 100 further includes multiple electrode devices, such as, for example rolling electrode devices 141, 142, 143, 144, adjacently positioned on the surface of the web 110 for measuring various electrical properties of a layer deposited onto the advancing web material 110. Typical electrical properties of a layer may include, for example, a resistance parameter and a capacitance parameter of the layer.

In one embodiment, the electrode devices 141 through 144 are in contact with the web material 110 to form a 4-point probe, which measures a resistance parameter at the probe as a function of the thickness, structure, and composition of the web 110. In the 4-point probe shown in FIG. 1, a current having a predetermined intensity value $\Delta I$ is forced into a layer 150 of the web material 110 from the outer electrode device 141 to the outer electrode device 144 and the voltage drop value $\Delta V$ is measured at the inner electrode devices 142 and 143. Thus, the resistance parameter R can be calculated as $R = \Delta V / \Delta I$.

In an alternative embodiment shown in FIG. 1, rolling electrode devices 131 and 132 are adjacently positioned on the surface of the web material 110 and in contact with the layer 150 of the web material 110 to form a 2-point probe, which measures the resistance parameter R between the two devices 131, 132, as described in further detail below.

Figure 2:
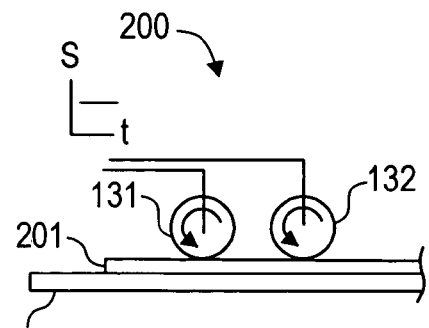
FIG. 2 illustrates a perspective view of an apparatus for measuring and monitoring layer properties in web-based processes within the system, according to one embodiment of the invention.

FIG. 2 illustrates a perspective view of an apparatus for measuring and monitoring layer properties in web-based processes within the system 100, according to one embodiment of the invention. As illustrated in FIG. 2, the apparatus 200 includes rolling electrode devices 131 and 132 adjacently positioned onto a layer 201 deposited upon a substrate 202, which advances in the direction of the arrow and enables the rolling electrode devices 131, 132 to rotate, as shown in FIG. 2. In one embodiment, the layer 201 and the substrate 202 form the web material 110 shown in FIG. 1. The rolling electrode devices 131, 132 continuously measure electrical parameters of the layer 201 and provide a constant electrical signal to a layer deposition system (not shown) for further adjustment of layer thickness, composition, and impurity levels. In one embodiment, the outer surface of the electrode devices 131, 132 is conductive, such as, for example, fabricated out of metal, or any other known conductive material capable of performing continuous measurements of the electrical parameters of the layer 201.

Figure 3:
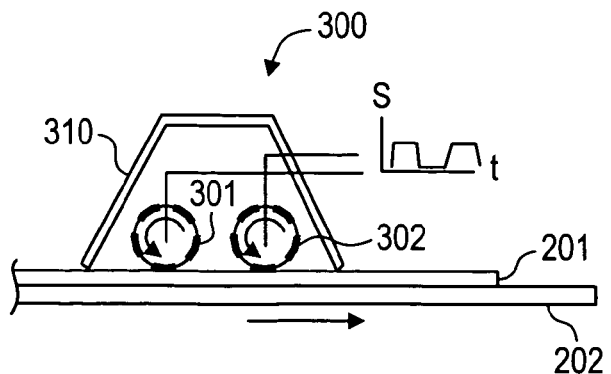
FIG. 3 illustrates a perspective view of an apparatus for measuring and monitoring layer properties in web-based processes within the system, according to an alternative embodiment of the invention.

FIG. 3 illustrates a perspective view of an apparatus for measuring and monitoring layer properties in web-based processes within the system 100, according to an alternative embodiment of the invention. As illustrated in FIG. 3, the apparatus 300 includes rolling electrode devices 301 and 302 adjacently positioned onto a layer 201 deposited upon a substrate 202, which advances in the direction of the arrow and enables the rolling electrode devices 301, 302 to rotate.

As shown in the alternative embodiment of FIG. 3, the outer surface of each electrode device 301, 302 includes alternating portions of a first material, such as, for example, a conductive material (metal), and a second material, such as, for example, an insulating material, respectively. The rolling electrode devices 301, 302 provide a modulated electrical signal S by shifting the measurement frequency from a low frequency near a high noise region to a higher frequency and narrow band to provide increased immunity to noise. In an alternative embodiment, if the apparatus 300 is located in the vicinity of a noise source or plasma, the apparatus 300 may further include a grounded shield structure 310 capable of attenuating the noise and, thus, avoiding corruption of the modulated electrical signal S.

In one embodiment, the rolling electrode devices 301, 302 are arranged in equally spaced configurations, such that the measurement frequency is in a noise minimum range of the web processing environment. Alternatively, the rolling electrode devices 301, 302 may be arranged in a pseudo-random pattern of conductive and nonconductive regions shaped to provide a pseudo-random signal sequence and to provide broadband immunity from noise that is apt to be present within the web, due to other web processing during the advancement of the web material.

Figure 4:
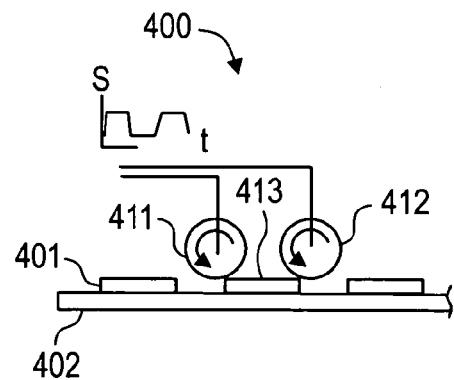
FIG. 4 illustrates a perspective view of an apparatus for measuring and monitoring layer properties in web-based processes within the system, according to another alternative embodiment of the invention.

FIG. 4 illustrates a perspective view of an apparatus for measuring and monitoring layer properties in web-based processes within the system 100, according to another alternative embodiment of the invention. As illustrated in FIG. 4, the apparatus 400 includes rolling electrode devices 411 and 412 adjacently positioned onto a patterned layer 401 deposited onto a substrate 402, which advances in the direction of the arrow and enables the rolling electrode devices 411, 412 to rotate, as shown in FIG. 4. In one embodiment, the layer 401 is patterned and the distance between the electrode devices 411 and 412 is selected to be equal or lower than the width of each stripe 413 within the layer 401. As a result, the electrode devices 411, 412 are in intermittent contact with the layer 401 and, thus, the resulting electrical signal S is modulated and can be used to measure the electrical properties of the layer 401. In addition, if the resulting electrical signal S is compared to the position of the layer 401 and to an expected signal, the geometric structure of the layer 401 may be compared to an expected structure, resulting in corrective actions being taken should measurable discrepancies arise.

Figure 5:
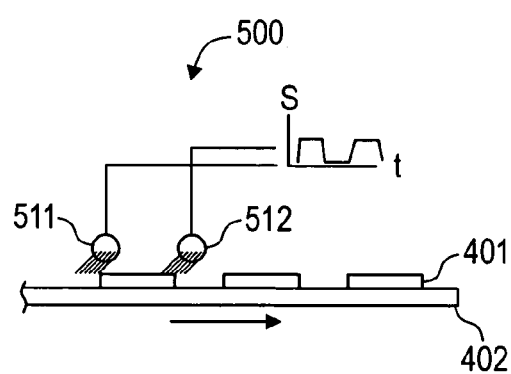
FIG. 5 illustrates a perspective view of an apparatus for measuring and monitoring layer properties in web-based processes within the system, according to yet another alternative embodiment of the invention.

FIG. 5 illustrates a perspective view of an apparatus for measuring and monitoring layer properties in web-based processes within the system, according to yet another alternative embodiment of the invention. As illustrated in FIG. 5, the apparatus 500 includes electrode devices 511 and 512 adjacently positioned onto the patterned layer 401 coupled to the substrate 402, which advances in the direction of the arrow. In one embodiment, the electrode devices 511, 512 are conductive brushes fabricated from one of many known conductive materials, such as, for example, carbon fibers or wires. As the substrate 402 advances, the electrode devices 511, 512 make intermittent contact with the patterned layer 401 and are used to measure the electrical properties of the layer 401.

Figure 6:
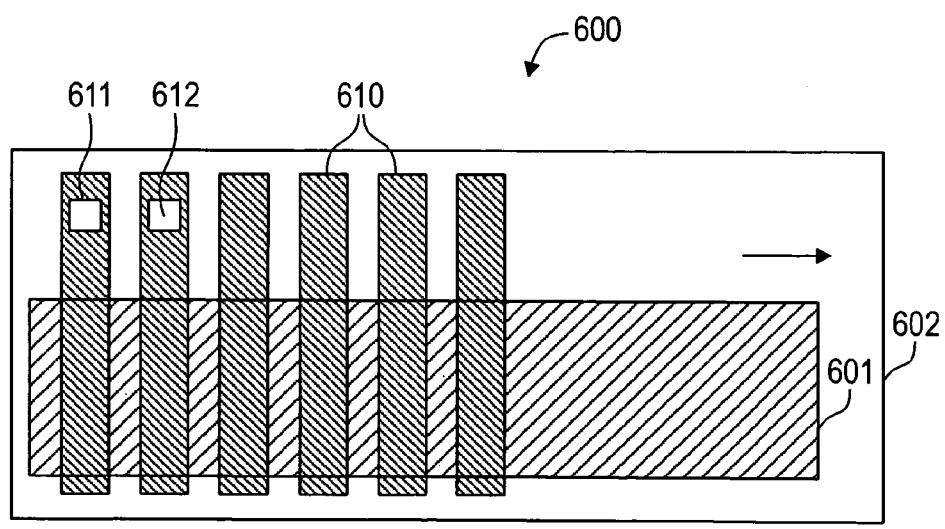
FIG. 6 illustrates a top view of an apparatus for measuring and monitoring layer properties in web-based processes within the system, according to yet another alternative embodiment of the invention.

FIG. 6 illustrates a top view of an apparatus for measuring and monitoring layer properties in web-based processes within the system 100, according to yet another alternative embodiment of the invention. As illustrated in FIG. 6, the apparatus 600 includes a plurality of patterned conductive electrodes 610, such as, for example, patterned metal electrodes, connected to a layer 601 to be measured, the layer 601 being deposited onto a substrate 602 advancing in the direction of the arrow. Multiple electrode devices 611, 612, such as, for example, rollers or conductive brushes, contact the patterned electrodes 610 intermittently and measure a resulting modulated electrical signal, which can be used in determining the electrical properties of the layer 601.

Figure 7:
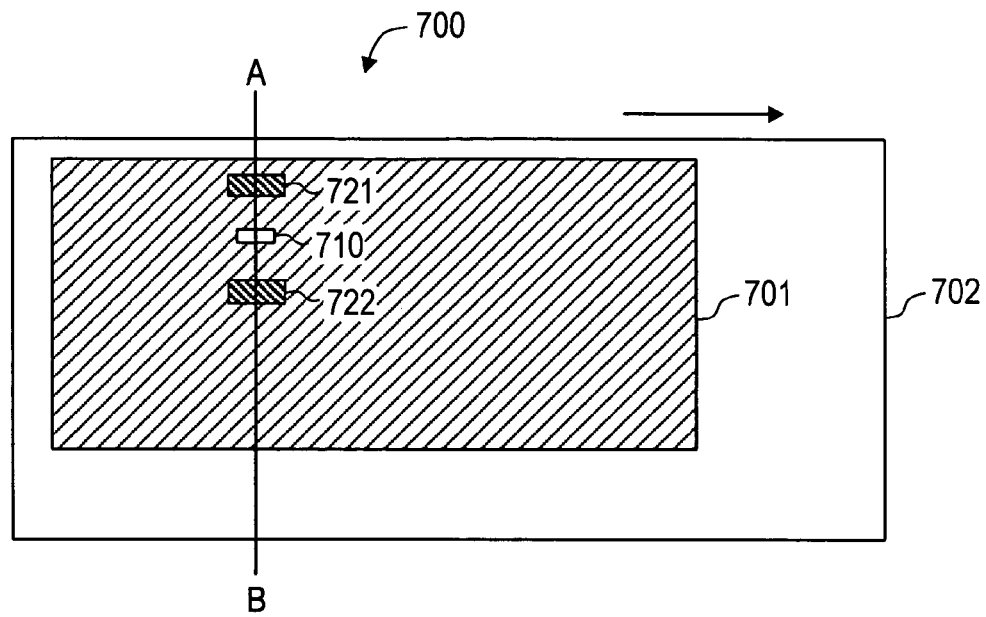
FIG. 7 illustrates a top view of an apparatus for measuring and monitoring layer properties in web-based processes within the system, according to yet another alternative embodiment of the invention.
Figure 8:
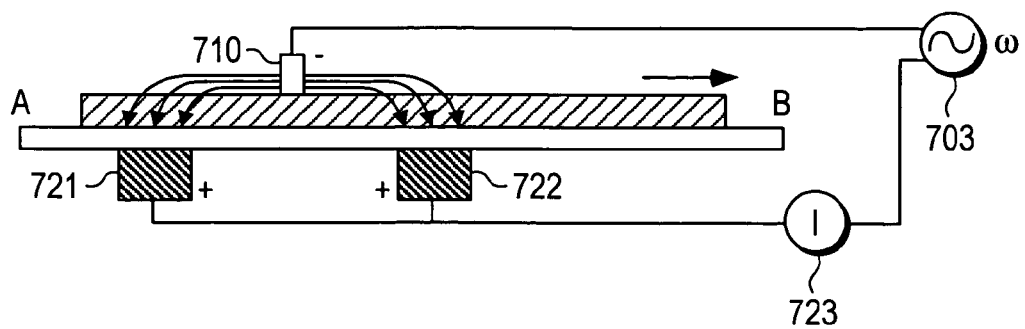
FIG. 8 illustrates a sectional view of the apparatus for measuring and monitoring layer properties in web-based processes shown in FIG. 7.

FIG. 7 illustrates a top view of an apparatus for measuring and monitoring layer properties in web-based processes within the system 100, according to yet another alternative embodiment of the invention. FIG. 8 illustrates a sectional view of the apparatus for measuring and monitoring layer properties in web-based processes shown in FIG. 7, the sectional view being taken along the A-B line. As illustrated in FIGS. 7 and 8, in one embodiment, the apparatus 700 includes a first topside electrode device 710, such as, for example, a rolling electrode device or a conductive brush, connected to the upper surface of a layer 701 adjacently positioned onto a non-conducting substrate 702 moving laterally in the direction of the arrow. The apparatus 700 further includes second backside electrode devices 721, 722 connected to the lower surface of the substrate 702.

As shown in FIG. 8, in one embodiment, an alternating voltage source 703 is coupled to the topside electrode device 710 and the backside electrode devices 721 and 722. As the substrate 702 and the layer 701 advance, the negative charge current at the topside electrode device 710, flows in synchronicity with the alternating voltage. Thus, the electrons will be attracted and will accumulate at the backside electrode devices 721 and 722, which have a positive charge. However, because the voltage is oscillating, once the polarity changes, the electrons will be subsequently attracted back to the topside electrode device 710.

In this embodiment, the capacitance value C of the structure is determined based on the size of the electrode devices 710, 721, and 722, the thickness of the deposited layer 701 and its dielectric constant. Alternatively, electrode devices 721 and 722 can be combined into one continuous electrode.

The capacitance can be measured by measuring the current flowing through the circuit comprised of the voltage source 703, the electrode device 710, the layers 701 and 702, the electrodes 721 and 722, and the current meter 723. At low frequencies, the alternating current flows from the topside electrode device 710 to the backside electrode devices 721 and 722, or vice-versa. As the frequency increases, the current measured by the current meter 723 decreases and, at sufficiently high predetermined frequency values, the alternating current eventually stops flowing from the topside electrode 710 to the backside electrodes 721 and 722.

In one embodiment, a measured midpoint critical frequency value "f," where induced current falls to half the low frequency amplitude, the electrical resistance R of the layer 701 can be calculated according to the formula:

$$R = 1/(2\pi)fC$$

This procedure works even if the substrate 702 is not conductive. The measurement determines the spreading resistance parameter of the layer 701 by measuring the frequency dependence of the distributed impedance of the structure.

Figure 9:
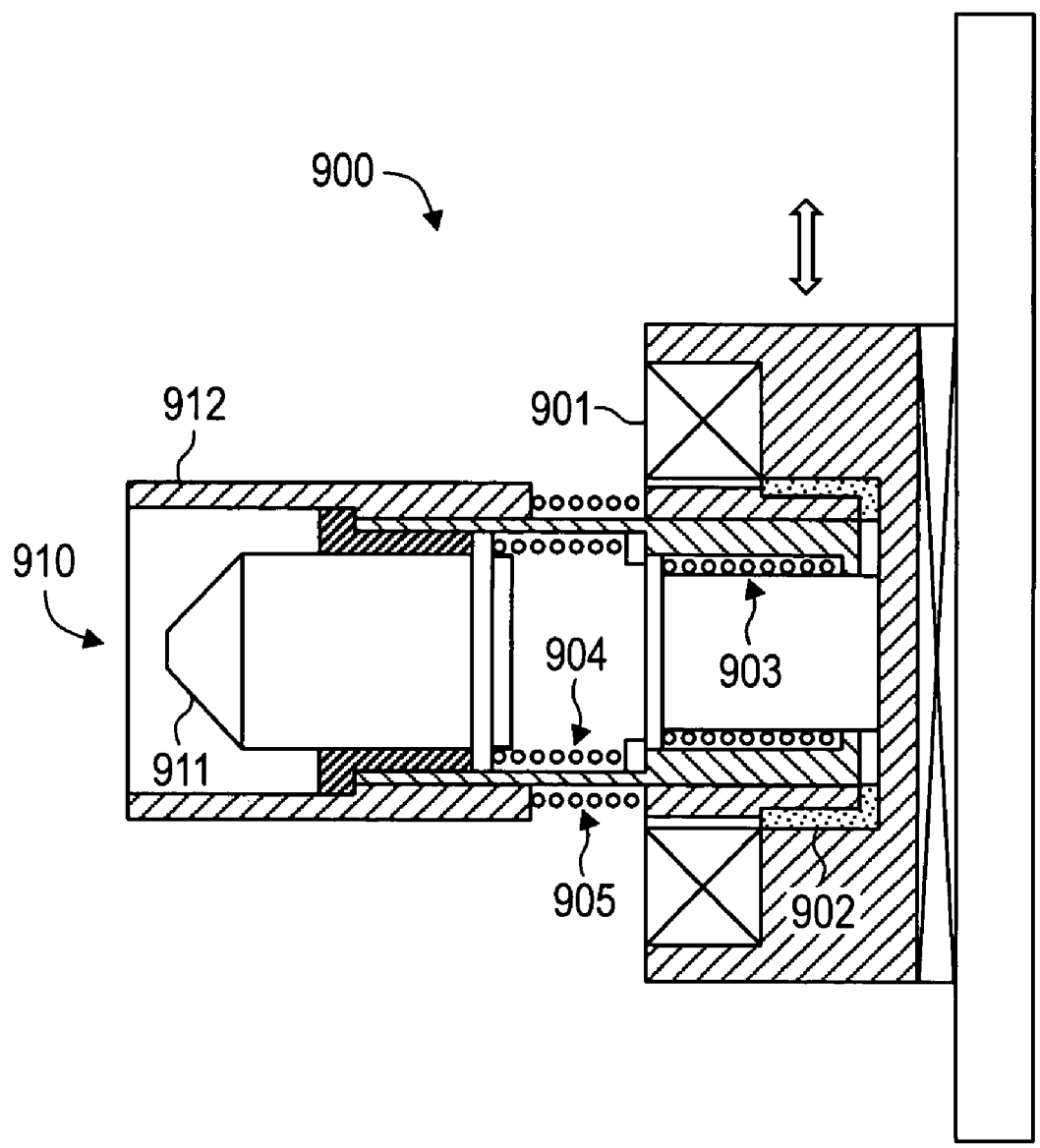
FIG. 9 illustrates a sectional view of a probe assembly mechanism for measuring and monitoring layer properties in web-based processes, according to one embodiment of the invention.

For slow processing speeds, where a layer of web material to be measured advances at a low speed, such as, for example, a speed of 6 (six) inches per minute required to produce a predetermined layer thickness, conventional probe assemblies, such as, for example, 4-point resistance measuring heads fabricated by KLA Tencor, of Santa Clara, Calif., Lucas Signatone, of Gilroy, Calif., and other manufacturers, may be used to perform measurements and monitoring of the desired electrical properties of the layer. FIG. 9 illustrates a sectional view of an exemplary probe assembly mechanism for measuring and monitoring layer properties in web-based processes, according to one embodiment of the invention. As illustrated in FIG. 9, the probe assembly 900 includes a probe head assembly 910, which further includes a probe head 911 and a mechanical shield 912, for measuring the resistance of the web material, a solenoid coil 901 and a solenoid armature 902 for activating the probe head assembly 910, and multiple springs, such as, for example a return spring 903, a probe spring 904, and a shield spring 905, each enabling engagement and disengagement of the probe assembly 900, as described in further detail below in connection with FIGS. 10A-D. Although the structure of the probe assembly 900 is described in great detail in connection with FIG. 9, it is to be understood, however, that other known probe assembly mechanisms may be used to perform the operations of the present invention.

Figure 10A:
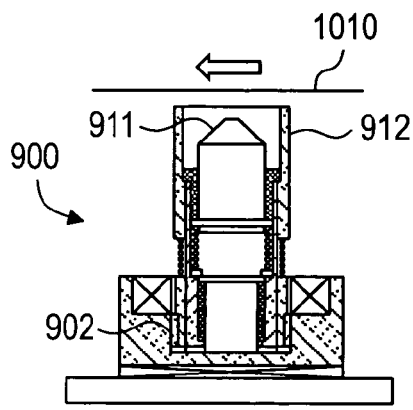
FIGS. 10A-D illustrate a measurement and monitoring sequence using the probe assembly mechanism shown in FIG. 9.

FIGS. 10A-D illustrate a measurement and monitoring sequence using the probe assembly mechanism shown in FIG. 9. As illustrated in FIG. 10A, a web material 1010 advances in the direction of the arrow. The solenoid coil 901 and the solenoid armature 902 within the probe assembly 900 are actuated and the probe head assembly 910 containing the probe head 911 and the mechanical shield 912 is energized to advance towards the moving web material 1010.

Figure 10B:
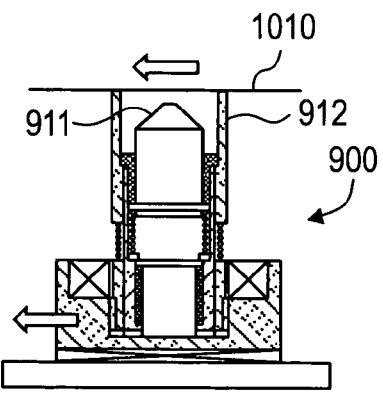

As illustrated in FIG. 10B, the mechanical shield 912 contacts the layer deposited onto the web material 1010, prompts the probe assembly 900 to start advancing in tandem with the web material 1010, and provides electrical shielding for the probe head 911. Subsequently, the probe assembly 900 and the web material 1010 advance together at the same speed rate. Meanwhile, the probe head 911 continues its advance towards the web material 1010.

Figure 10C:
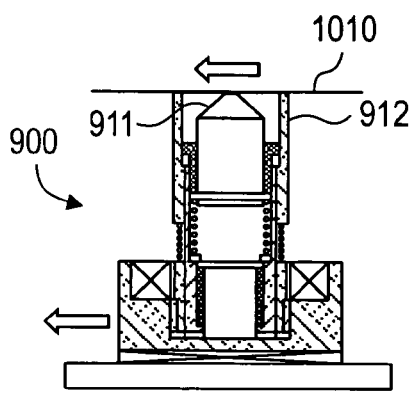
Figure 10D:
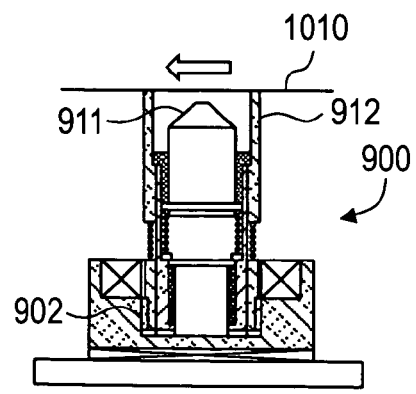

Next, as illustrated in FIG. 10C, the probe head 911 makes contact with the web material 1010 and measurement of the resistance parameter of the layer is initiated. Finally, as illustrated in FIG. 10D, once the measurement is complete, the solenoid armature 902 is de-energized, and the probe head 911 disengages from the web material 1010, which continues to advance in the direction of the arrow. The probe assembly 900 is subsequently retracted to its initial position to prepare for the next measurement operation.

Figure 11:
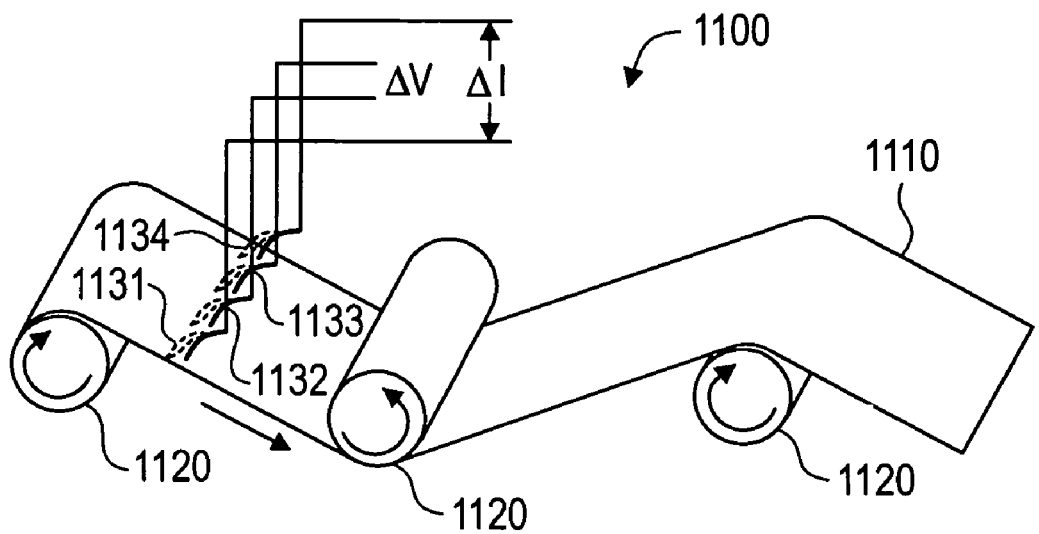
FIG. 11 illustrates a perspective view of a system for measuring and monitoring layer properties in web-based processes using compliant probes, according to one embodiment of the invention.

FIG. 11 illustrates a perspective view of a system for measuring and monitoring layer properties in web-based processes using compliant probes, according to one embodiment of the invention. As illustrated in FIG. 11, the system 1100 includes a web material 1110 and several conveyor modules 1120 positioned to turn and advance the web material 1110 in the direction of the arrow. In one embodiment, the system 1100 further includes multiple compliant probe devices, such as, for example probe devices 1131, 1132, 1133, 1134, adjacently positioned on the surface of the web 1110 for measuring various electrical properties of a layer deposited onto the advancing web material 1110.

In one embodiment, if the probe devices 1131 through 1134 are in contact with the web material 1110, they form a 4-point probe, which measures a resistance parameter at the probe as a function of the thickness, structure, and composition of the layer. In the 4-point probe shown in FIG. 11, a current having a predetermined intensity value ΔI is forced into a layer of the web material 1110 from the outer electrode devices 1131 to the outer electrode device 1134 and the voltage drop value ΔV is measured at the inner electrode devices 1132 and 1133. Thus, the resistance parameter R can be calculated as R=ΔV/ΔI.

The extension range of the probe devices 1131 through 1134 is selected such that it exceeds the motion of the web material 1110 during the predetermined time required for measurement. For example, typical measurement time scales of 0.1-1 seconds with web speeds of 0.25 centimeter/sec require the probe devices 1131 through 1134 to extend approximately 0.02-0.25 centimeters without slipping. In some cases, the compliant electrodes 1131 through 1134 can drag along the sample. In such cases, retracting and repositioning of the electrodes is not necessary.

Figure 12:
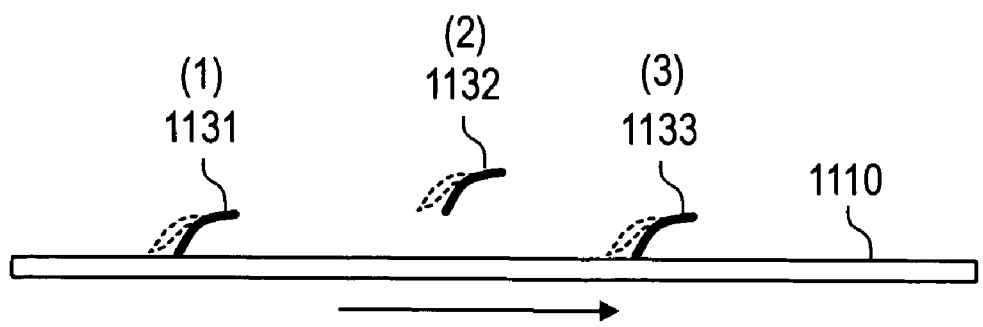
FIG. 12 illustrates a perspective view of the compliant probes within the system for measuring and monitoring layer properties in web-based processes shown in FIG. 11.

FIG. 12 illustrates a perspective view of the compliant probes within the system for measuring and monitoring layer properties in web-based processes shown in FIG. 11. As shown in FIG. 12, in an initial state (1), the compliant probe devices 1131 through 1134, of which only a sectional view of the probe device 1131 is shown, make contact with the web material 1110 and measurements are made. Next, at state (2), the compliant probe devices 1131 through 1134 are retracted and no measurements are performed. Finally, at state (3), the compliant probe devices 1131 through 1134 are activated again to make contact with the web material 1110 and to perform the next set of measurements.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An apparatus comprising:
a plurality of electrode devices adjacently positioned on a surface of a web material, said web material advancing with a predetermined speed;
said plurality of electrode devices to perform measurements of electrical parameters of a layer of said web material and to provide an electrical signal based on said measured electrical parameters to a layer deposition system for further adjustment of layer properties of said layer.

2. The apparatus according to claim 1, wherein said web material further comprises a substrate, said layer being deposited onto said substrate.

3. The apparatus according to claim 2, wherein said plurality of electrode devices further comprises a first electrode device coupled to a surface of said layer and at least one second electrode device coupled to a surface of said substrate.

4. The apparatus according to claim 3, further comprising an alternating voltage source coupled to said first electrode device and said at least one second electrode device to provide an alternating voltage signal, which enables a synchronous current flow between said first electrode device and said at least one second electrode device.

5. The apparatus according to claim 4, wherein an electrical resistance parameter of said layer is calculated based on a capacitance value determined as a function of said first electrode device, said at least one second electrode device, a thickness parameter and a dielectric constant of said layer.

6. The apparatus according to claim 1, wherein each electrode device of said plurality of electrode devices is a rolling electrode device.

7. The apparatus according to claim 6, wherein said each rolling electrode device contacts said layer of said web material to measure said electrical parameters and to provide said electrical signal.

8. The apparatus according to claim 7, wherein said plurality of rolling electrode devices further comprises at least two outer rolling electrode devices to receive a current having a predetermined intensity value and at least two inner rolling electrode devices to measure a voltage drop value based on said received current.

9. The apparatus according to claim 8, wherein said outer rolling electrode devices and said inner rolling electrode devices form a four-point probe to enable calculation of an electrical resistance parameter of said web material at said probe based on said predetermined intensity value of said current and said voltage drop value.

10. The apparatus according to claim 7, wherein said layer properties further comprise any of a thickness parameter, a composition parameter, and impurity levels of said layer.

11. The apparatus according to claim 7, wherein said plurality of rolling electrode devices further comprises at least two rolling electrode devices to perform continuous measurements of said electrical parameters.

12. The apparatus according to claim 11, wherein an outer surface of said each rolling electrode device comprises a conductive material to output a constant electrical signal for adjustment of said layer properties.

13. The apparatus according to claim 11, wherein an outer surface of said each rolling electrode device comprises alternating portions of a first material and a second material to output a modulated electrical signal for adjustment of said layer properties.

14. The apparatus according to claim 11, further comprising a grounded shield structure positioned over said rolling electrode devices to attenuate background signals.

15. The apparatus according to claim 11, wherein said each rolling electrode device further comprises a pseudo-random pattern of conductive and non-conductive regions to provide a pseudo-random electrical signal sequence and broadband immunity from noise within said web material.

16. The apparatus according to claim 1, wherein each electrode device of said plurality of electrode devices is a conductive brush making intermittent contact with said layer to measure said electrical parameters and to provide said electrical signal.

17. The apparatus according to claim 1, wherein said layer is continuous to enable said plurality of adjacent electrode devices to output a constant electrical signal.

18. The apparatus according to claim 1, wherein said layer is patterned to enable said plurality of adjacent electrode devices to output a modulated electrical signal.

19. The apparatus according to claim 1, further comprising a plurality of patterned electrodes coupled to said layer and in contact with each electrode device of said plurality of electrode devices.

20. The apparatus according to claim 1, wherein each electrode device of said plurality of electrode devices is a probe device having an extension value selected to exceed a motion of said web material in a predetermined time period.

21. The apparatus according to claim 20, wherein said each probe device successively contacts said layer of said web material during said predetermined time period to measure said electrical parameters and to provide said electrical signal and retracts subsequent to each contact with said layer.

* * * * *